(12) United States Patent
Crockford

(10) Patent No.: US 11,426,124 B2
(45) Date of Patent: Aug. 30, 2022

(54) DETERMINING THE ARTERIAL STRUCTURE OF THE HAND

(71) Applicant: Digital & Future Technologies Limited, Colchester (GB)

(72) Inventor: Christopher John Crockford, Lancashire (GB)

(73) Assignee: DIGITAL & FUTURE TECHNOLOGIES LIMITED, Colchester (GB)

(*) Notice: Subject to any disclaimer, the term of this patent is extended or adjusted under 35 U.S.C. 154(b) by 448 days.

(21) Appl. No.: 16/427,860

(22) Filed: May 31, 2019

(65) Prior Publication Data

US 2019/0365323 A1 Dec. 5, 2019

(30) Foreign Application Priority Data

May 31, 2018 (GB) .................................... 1808951

(51) Int. Cl.
*A61B 5/00* (2006.01)
*A61B 5/021* (2006.01)
*A61B 5/318* (2021.01)
*A61B 5/024* (2006.01)

(52) U.S. Cl.
CPC ........ *A61B 5/6826* (2013.01); *A61B 5/02125* (2013.01); *A61B 5/318* (2021.01); *A61B 5/02427* (2013.01); *A61B 5/02438* (2013.01)

(58) Field of Classification Search
None
See application file for complete search history.

(56) References Cited

U.S. PATENT DOCUMENTS

| | | | |
|---|---|---|---|
| 2005/0143640 A1* | 6/2005 | Hoctor | A61B 8/04 600/407 |
| 2008/0039731 A1* | 2/2008 | McCombie | A61B 5/02255 600/485 |
| 2017/0119265 A1* | 5/2017 | Hill | A61B 5/7475 |
| 2017/0367594 A1* | 12/2017 | Gu | A61B 5/318 |
| 2018/0146870 A1* | 5/2018 | Shemesh | A61B 5/02438 |
| 2018/0317784 A1* | 11/2018 | Albert | A61B 5/681 |
| 2019/0175142 A1* | 6/2019 | Takamatsu | A61B 8/488 |

FOREIGN PATENT DOCUMENTS

EP 3073905 10/2016

* cited by examiner

*Primary Examiner* — Yi-Shan Yang
(74) *Attorney, Agent, or Firm* — Occhiuti & Rohlicek LLP

(57) ABSTRACT

An apparatus for determining the arterial structure of the hand of a subject, the apparatus comprising a wrist pulse measurement device configured to measure wrist pulse signals at the wrist of the subject, a digit pulse measurement device configured to measure digit pulse signals at the digits of the hand, the apparatus being configured to compare the arrival time of one or more waveform features in a wrist pulse signal and the arrival time of the corresponding feature in two or more digit pulse signals in order to determine a pulse transit time for each of the one or more waveform features, thereby estimating the arterial structure of the hand.

17 Claims, 3 Drawing Sheets

DETERMINING THE ARTERIAL STRUCTURE OF THE HAND

CROSS-REFERENCE TO RELATED APPLICATIONS

This application claims priority to Great Britain No. 1808951.6 filed on May 31, 2018, the contents of which are hereby incorporated by reference in their entirety.

FIELD

This invention relates to apparatus and methods for determining the arterial structure of the hand.

BACKGROUND

Blood pressure is an important parameter as high blood pressure (hypertension) puts extra strain on the heart and arteries, which may cause arteries to become thicker and less flexible, or to become weaker. Weaker arteries may become narrow over time or burst, potentially leading to a heart attack or a stroke. Low blood pressure (hypotension) can lead to dizziness and light-headedness and may be indicative of a more serious medical problem.

Existing systems for monitoring cardiovascular health use electrocardiogram (ECG) or photoplethysmogram (PPG) techniques to measure pulse signals. In an ECG, electric sensors attached to the skin are used to detect the electrical signals produced by the heart each time it beats. A PPG reading can be obtained through optronics, normally a light-emitting diode (LED) and a photodiode pair operating in green, red or infrared wavelength ranges. The LED illuminates the skin and then the amount of light either transmitted or reflected is measured by the photodiode. During each cardiac cycle, a pressure pulse reaches the skin and distends the arteries and arterioles therein, resulting in a measurable change in light transmission/reflection in the of the skin.

The popularity of smartphones and smartwatches has led to the development of applications for these devices in the fields of personal fitness and telemedicine. Smartwatches and wrist-worn personal fitness devices have begun to utilise ECG and PPG sensors and smartphone cameras have been used to take PPG readings. However, such devices typically suffer from poor performance due to movement artefacts in the measurements.

When a pulse wave arrives at a bifurcation in the vascular system, a certain amount of the wave will be reflected back. This reflected wave will travel back to the aorta. This can be problematic if a reflected wave arrives at the aorta during diastole, the period where the aorta should be rest prior to the next systolic phase, as ejecting blood into a quivering aorta can lead to increased ventricular pressure during systole and reduced diastolic pressure. In turn, this can lead to an increased risk of cardiovascular events. In general, the faster a pulse pressure wave travels, the higher the chance for reflected waves to return to the aorta during diastole is. The behaviour of pulse waves at bifurcations is poorly understood and difficult to measure.

Existing circulation tests for the hands and arms include Allen's test. Allen's test is performed by clinicians and physiotherapists looking for abnormal circulation. The procedure involves: asking a patient to clench their fist for a time period; applying manual compression to the radial and ulnar arteries; asking a patient to relax the hand; releasing pressure over one of the radial or ulnar artery. If colour returns quickly to the hand, this suggest adequate flow from the uncompressed artery. The manual nature of such a test makes it unreliable and its clinical significance is unproven.

There is a need for methods that at least partially address some of these problems.

SUMMARY OF THE INVENTION

According to the present invention there is provided an apparatus for determining the arterial structure of the hand of a subject, the apparatus comprising a wrist pulse measurement device configured to measure wrist pulse signals at the wrist of the subject, a digit pulse measurement device configured to measure digit pulse signals at the digits of the hand, and the apparatus being configured to compare the arrival time of one or more waveform features in a wrist pulse signal and the arrival time of the corresponding feature in two or more digit pulse signals in order to determine a pulse transit time for each of the one or more waveform features, thereby estimating the arterial structure of the hand.

The apparatus may be further configured to use an expected pulse transit time to associate a wrist pulse signal with the two or more digit pulse signals.

The expected pulse transit time may be the average time taken for a pulse to travel between the wrist and the digits of an adult.

The expected pulse transit time may be estimated using one or more of the height, weight, age and hand size of the subject.

The wrist pulse signal measurement device and the digit pulse measurement device may be configured to measure pulse signals with respect to a common time signal.

The apparatus may be further configured to, if only one waveform feature is detected in a digit pulse signal, vary the expected pulse transit time until two waveform features are detected.

The apparatus may be further configured to calculate a pulse wave velocity for each of the waveform features by dividing an estimated arterial path length by the pulse transit time of that feature.

The estimated arterial path length for each waveform feature may be the average arterial path length for an adult between the wrist and the digit at which the feature is measured.

The estimated arterial path length for each waveform feature may be estimated using one or more of the height, weight, age and hand size of the subject.

The apparatus may be further configured to determine that the arterial structure is atypical if it is determined that one of the pulse wave velocities calculated for a waveform feature significantly deviate from the pulse wave velocities calculated for the other waveform features.

The apparatus may be further configured to determine that one of the pulse wave velocities calculated for each a waveform feature significantly deviates from the pulse wave velocities calculated for the other waveform features if it is more than 1, 2 or 3 standard deviations away from the mean of all of the calculated pulse wave velocities.

The apparatus may be further configured to, if it is determined that one of the pulse wave velocities calculated for a waveform feature significantly deviates from the pulse wave velocities calculated for the other waveform features, calculate a corrected arterial path length to replace the estimated arterial path length used to calculate the significantly deviating pulse wave velocity using the average of the pulse wave velocities calculated for the other waveform features.

The apparatus may be further configured to compare each of the pulse wave velocities with known values to determine whether the pulse wave velocities correspond to a known arterial structure of the hand.

The apparatus may be further configured to refine the estimate of the arterial structure of the hand using the time of arrival of a reflected pulse waveform.

The apparatus may be further configured to determine location of waveform collision points in the palmar arches in dependence on the deviation from expected values of the time of arrival of one or more of reflected pulse waveforms and pulse waveforms spawned by pulse waveforms colliding in the one or more of the palmar arches.

The wrist pulse measurement device may comprise a photoplethysmography sensor. Estimating the arterial structure of the hand may comprise estimating the number of arteries present in the wrist. The apparatus may be further configured to normalise the number the wrist pulse signal with respect to the number of arteries present in the wrist.

The wrist pulse signal measurement device may comprise an electrocardiography sensor.

Estimating the arterial structure of the hand may comprise estimating one or more of the number of arteries present, which arteries are present, the number of and location or arterial branches.

The wrist pulse measurement device may comprise a smartwatch.

The digit pulse measurement device may comprise a smartphone.

There is also provided a method of determining the arterial structure of the hand of a subject, the method comprising measuring a wrist pulse signal at the wrist of the subject, measuring two or more digit pulse signals, each digit pulse signal being measured at a respective digit of the hand, comparing the arrival time of one or more waveform features in a wrist pulse signal and the arrival time of the corresponding feature in each of the digit pulse signals in order to determine a pulse transit time for each of the one or more waveform features, thereby estimating the arterial structure of the hand.

The method may further comprise using an expected pulse transit time to associate a wrist pulse signal with the two or more digit pulse signals.

The expected pulse transit time may be the average time taken for a pulse to travel between the wrist and the digits of an adult.

The method may further comprise estimating the expected pulse transit time using one or more of the height, weight, age and hand size of the subject.

The method may further comprise measuring the wrist pulse signal and the two or more digit pulse signals with respect to a common time signal.

The method may further comprise, if only one waveform feature is detected in a digit pulse signal, varying the expected pulse transit time until two waveform features are detected.

The method may further comprise calculating a pulse wave velocity for each of the waveform features by dividing an estimated arterial path length by the pulse transit time of that feature.

The estimated arterial path length for each waveform feature may be the average arterial path length for an adult between the wrist and the digit at which the feature is measured.

The method may further comprise estimating the estimated arterial path length for each waveform feature using one or more of the height, weight, age and hand size of the subject.

The method may further comprise, if it is determined that one of the pulse wave velocities calculated for a waveform feature significantly deviate from the pulse wave velocities calculated for the other waveform features, indicating the presence of an atypical hand arterial structure.

The method may further comprise determining that one of the pulse wave velocities calculated for each a waveform feature significantly deviates from the pulse wave velocities calculated for the other waveform features if it is more than 1, 2 or 3 standard deviations away from the mean of all of the calculated pulse wave velocities.

The method may further comprise, if it is determined that one of the pulse wave velocities calculated for a waveform feature significantly deviate from the pulse wave velocities calculated for the other waveform features, using the average of the pulse wave velocities calculated for the other waveform features to calculate a corrected arterial path length to replace the estimated arterial path length used to calculate the significantly deviating pulse wave velocity.

The method may further comprise comparing each of the pulse wave velocities with known values to determine whether the pulse wave velocities correspond to a known arterial structure of the hand.

The method may further comprise taking digit pulse measurements at one or more of the thumb, the thumb side of the index finger, and the outside of the little finger.

The method may further comprise refining the estimate of the arterial structure of the hand using the time of arrival of a reflected pulse waveform.

The method may further comprise using the deviation from expected values of the time of arrival of one or more of reflected pulse waveforms and pulse waveforms spawned by pulse waveforms colliding in the one or more of the palmar arches to determine the location of waveform collision points in the palmar arches.

The method may further comprise occluding one or more of the radial, ulnar and median arteries during the measurement of the wrist and digit pulse measurements.

The wrist pulse signal and the two or more hand pulse signals may comprise photoplethysmogram signals. Estimating the arterial structure of the hand may comprise estimating the number of arteries present in the wrist. The wrist pulse signal is normalised with respect to the number of arteries present in the wrist.

The wrist pulse signal may comprise an electrocardiogram signal.

Estimating the arterial structure of the hand may comprise estimating one or more of the number of arteries present, which arteries are present, the number of and location or arterial branches.

DESCRIPTION OF THE DRAWINGS

The present invention will now be described by way of example with reference to the accompanying drawings. In the drawings.

DETAILED DESCRIPTION

The following description is presented to enable any person skilled in the art to make and use the invention and is provided in the context of a particular application. Various modifications to the disclosed embodiments will be readily apparent to those skilled in the art.

The general principles defined herein may be applied to other embodiments and applications without departing from the spirit and scope of the present invention. Thus, the present invention is not intended to be limited to the embodiments shown but is to be accorded the widest scope consistent with the principles and features disclosed herein.

Figure 1:
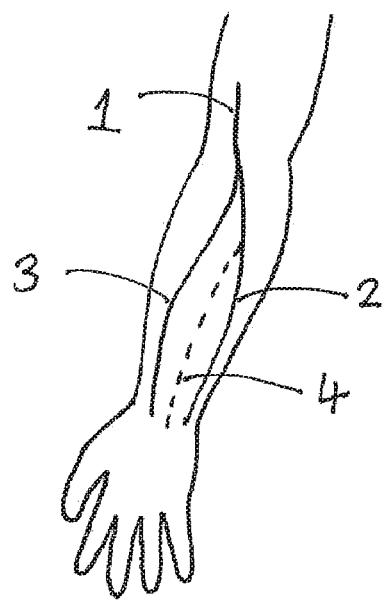
FIG. 1 shows a simplified diagram of the major arteries in the arm.

FIG. 1 is a schematic illustration showing the locations of the arteries in the arm. The brachial artery 1 divides below the elbow into the two arteries that serve the hand, the ulnar artery 2 and the radial artery 3. In roughly 8% of individuals there is also a third artery, the median artery 4 (depicted as a dotted line). The median artery is shown branching off the ulnar artery in FIG. 1, though instances of it branching off the radial artery also occur in some individuals.

Figure 2:
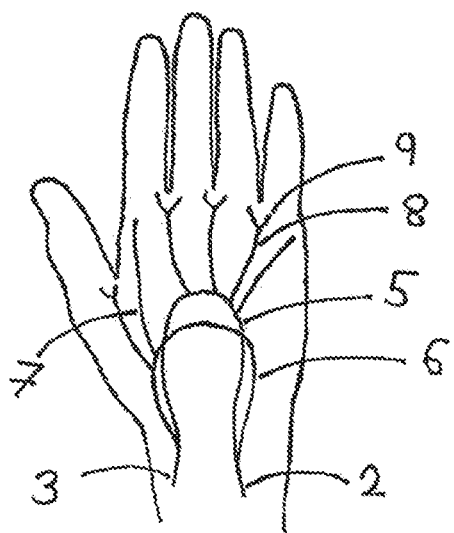
FIG. 2 shows a simplified diagram of the major arteries in the hand.

FIG. 2 shows a simplified diagram of the locations of the arteries in the hand. The ulnar and radial arteries both usually feed the superficial palmar arch 5 and the deep palmar arch 6. The deep palmar arch feeds the radial artery of the index finger 7, the thumb through the princeps pollicis, and three of the common palmar digital arteries 8, while the superficial palmar arch 5 feeds all of the common palmar digital arteries 8. The common palmar digital arteries 8 go on to feed the proper palmar digital arteries 9. For the purposes of clarity, this simplified view neglects blood vessels that are not pertinent to the present discussion. Though the arterial arrangement shown in FIG. 2 is the most common, as with the example of the median nerve above, individuals may have significantly different arrangements of arteries within the hand from what is shown in this figure. For example, the superficial palmar arch is complete (with branches to all digits) in 80% of individuals.

The Moens-Korteweg equation provides an estimate of the pulse wave velocity (i.e. the speed at which the pressure pulse propagates through the blood) by modelling the arteries as elastic tubes. Analysis can show that the pulse wave velocity (PWV) may be dependent on blood pressure according to the equation:

$$PWV = \sqrt{\frac{Ehe^{\gamma P}}{2r\rho}} \quad (1)$$

where E is the Young's modulus of the arteries, h is the arterial thickness, r is the arterial radius, ρ is the density of the blood, γ is a constant and P is the blood pressure. This equation can be re-arranged in terms of the blood pressure as:

$$P = \frac{1}{\gamma}\left(\frac{2r\rho PWV^2}{Eh}\right) = \frac{1}{\gamma}[2\ln(PWV) + \ln(2r\rho) - \ln(Eh)]. \quad (2)$$

It has been appreciated that, in practice, the PWV is difficult to measure non-intrusively, and that an improved approach is to substitute the PWV for the pulse transit time (PTT) and a corresponding length, L, travelled by the wave over that time, i.e. PWV=L/PTT.

The equation for the blood pressure then becomes:

$$P = \frac{1}{\gamma}\left[2\ln\left(\frac{L}{PTT}\right) + \ln(2r\rho) - \ln(Eh)\right] = \quad (3)$$
$$\frac{1}{\gamma}[2\ln(L) - 2\ln(PTT) + \ln(2r\rho) - \ln(Eh)].$$

The values of L, r, ρ, E, h and γ are constants for a given user (though may vary from user to user). Thus, Equation 3 demonstrates that the blood pressure scales as the logarithm of PTT. Thus, obtaining an accurate measure of the pulse transit time, or time interval, between two reference points along an artery can be used to obtain a measure of a user's blood pressure.

Figure 4:
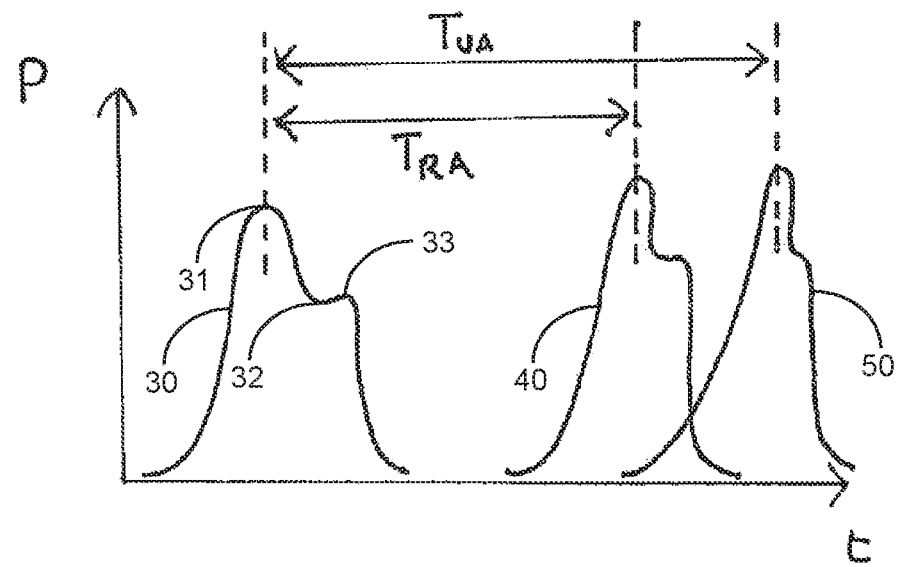
FIG. 4 shows an example combined wrist and digit plot of pulse pressure against time.

With regard to determining the arterial structure of the hand, the wrist and the digits serve as useful reference points. By taking measurements at the wrist and at various locations on the digits, useful comparative pulse signal data can be obtained. FIG. 4 shows a combined plot of a pulse signal taken at the wrist and at a digit, in this instance both measurements are blood pressure readings taken by PPG sensors. The waveforms 30, 40, 50 shown each comprise a systolic peak 31, a dicrotic peak 33 and a dicrotic notch 32 located between the systolic and dicrotic peaks 31 and 33. The systolic peak 31 is the peak of a systolic wave forming part of the waveform, and the dicrotic peak 33 is the peak of a dicrotic wave forming part of the waveform. Depending on where the pulse wave is measured on a user's body, the pressure waveform may include reflections of the pressure pulse. The reflections may be generated by changes in the peripheral vascular resistance at positions where the blood vessels branch from larger arteries to smaller arterioles and capillaries. Reflected waves are often smaller than the pressure pulses (as the incident waves are not fully reflected) and may not always be directly visible in the waveform. For example, the systolic peak reflection is typically smaller than the corresponding systolic peak. This can make the peaks of the reflected waves more difficult to observe, particularly for sensors suffering from measurement noise (as may be the case for PPG sensors in a practical implementation). This may make it difficult to obtain an accurate measurement of a user's blood pressure waveform using a single reading.

Figure 3:
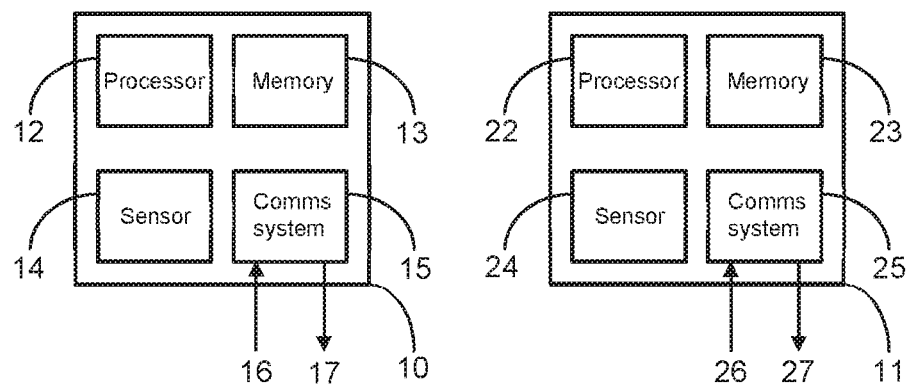
FIG. 3 shows components of an exemplary measurement apparatus.

FIG. 3 shows an example apparatus for taking measurements of a user's pressure waveform. The apparatus comprises a first measurement device 10 and a second measurement device 11. Each of measurement devices 10 and 11 could be, for example, a smartwatch, smartphone, adhesive patch, item of clothing, a digit-mounted-device containing one or more PPG sensors etc. Each of measurement devices 10 and 11 may be of the same device type, or different device types. One of devices 10 and 11 may be used for taking the wrist measurement (i.e. taking the pressure waveform measurements at the wrist) and the other of devices 10 and 11 may be used for taking the digit measurement (i.e. taking the pressure waveform measurement at the digit).

For the purposes of illustration, in this example measurement device 10 is taken to be a smartphone, and measurement device 11 is taken to be a smartwatch. Furthermore, in this example arrangement, the smartwatch 11 is used to take the wrist measurement while the smartphone 10 is used to take the digit measurements. However, in other examples the smartphone 10 may be used to take the wrist measurement while the smartwatch 11 may be used to take the digit measurements.

Each measurement device 10 and 11 comprises a processor, memory, sensor and communications system. More specifically, measurement device 10 comprises processor 12; a set of one or more sensors 14; memory 13 and communication system 15. Measurement device 11 comprises processor 22; a set of one or more sensors 24; memory 23 and communications system 25. The processor and memory of each device 10,11 may form a generic computer architecture. Memories 13 and 23 may store in a non-transitory way computer-readable instructions that can be executed by processors 12 and 22 respectively to perform the methods described herein.

The processing described below, i.e. any operations performed on data, are performed by a processor. Reference to operations performed by 'a/the processor' should be understood to relate to operations carried out by processor 12, processor 22, a processing unit external to devices 10 and 11, or some combination of these. A processing unit that is external to devices 10 and 11 will generally be in communication with both devices 10 and 11, and may comprise a PC, laptop or tablet, or a further smartphone or smartwatch.

The sensors 14 of device 10 include one or more PPG sensors configured to take the digit measurements to obtain a measurement of the user's blood pressure waveform in their fingertips by illuminating the skin and tracking changes of light absorption over time. The PPG sensors thus track changes in the blood volume at the site of measurement (in this case the fingertips) over time. The sensors 14 may include additional sensors to provide additional signals; for example the sensors 14 may additionally include one or more ECG sensors for taking ECG readings to provide ECG signals.

The sensors 24 of device 11 include one or more PPG sensors configured to take wrist measurements to obtain a measurement of the user's blood pressure waveform at their wrist by illuminating the skin and tracking changes of light absorption over time. The PPG sensors thus track changes in the blood volume at the site of measurement (in this case the wrist) over time. Measurements taken at the wrist may be taken on the top surface (i.e. the side corresponding to the back of the hand) or the bottom surface (i.e. the side corresponding to the palm of the hand).

The communications systems 15, 25 of each device 10 and 11 respectively enables input signals 16, 26 and output signals 17, 27 respectively to be transferred to and from each device. Each communications system may comprise a wired connection, such as any generic serial or parallel interfaces. The communications system may provide a USB, micro-USB or ethernet connection, for example. The communications system may comprise a wireless communication module such as Wi-Fi, Bluetooth®, radio or optical systems.

In order to combine the wrist and digit data, a pulse wave measured at the wrist (e.g. by device 11) is associated with a pulse wave measured at a digit (e.g. by device 10). In other words, pulse wave measurements taken by device 10 are associated with, e.g. mapped to, pulse wave measurements taken by device 11. Associating a pulse wave measured at the wrist with a pulse wave measured at the digit indicates both measurements are of the same pulse wave, measured at the two sites of the wrist and digit.

An expected pulse transit time across the hand from the wrist to the digit can be used to associate pulse waves measured by device 10 with pulse waves measured by device 11. The expected pulse transit time is the time after which a pulse wave detected at the wrist is expected to arrive at the digit. The expected pulse transit time may be the average time for a pulse to travel between the wrist and the digits of a healthy adult. An estimate of the expected pulse transit may be found using biometric information about the user, such as one or more of user height, weight, age and hand size. This biometric information may be input into one or both of devices 10 and 11. The information may for example be input manually by the user. The processor of the device that receives the biometric information may then calculate an expected pulse transit time in dependence on the received biometric information.

The process of associating digit pulse waves with wrist pulse waves can be simplified by having the measurement devices 10 and 11 measure the pulse signal with respect to a common time signal, for example by using a common clock or synchronised clocks. Once an expected pulse transit time is determined, the digit data in a time window can be isolated. The time window will be centred at the time of a pulse wave detected at the wrist plus the expected pulse transit time. The time window should at least be wide enough to incorporate an entire pulse wave period but will generally be wider than this in order to capture two narrowly separated peaks, such as those on the right side of FIG. 4. Though we refer to peaks herein and label the peaks in FIG. 4, any other waveform feature may be used, such as rising or falling edges, troughs, points of inflection or an arbitrary point.

Thus, in summary, the following steps may be performed to associate a pulse wave measured at the user's wrist with a pulse wave measured at the user's digit:

1) measure one or more pulse waves at the user's wrist using device 11, and one or more pulse waves at the user's digit using device 10, the devices 10 and 11 using a synchronised time signal to measure the pulse waves. The measured pulse waves may be recorded in memories 13 and 23 of devices 10 and 11 respectively.

2) for a selected pulse wave measured by one of devices 10 and 11, using the expected pulse transit time between the wrist and digit to identify an associated pulse wave measured by the other of devices 10 and 11. The associated pulse wave may be chosen to be the pulse wave having a time value that most closely matches the time value of the selected pulse wave offset by the expected pulse transit time. The time value for a pulse wave may be a characteristic time value: e.g. the leading time value of the pulse wave (i.e. the time value the pulse wave is measured to begin); the trailing time value of the pulse wave (i.e. the time value the pulse wave is measured to finish); the mean time value of the pulse wave etc. Step 2 may be performed by one of processors 12 and 22, or by some other external device in communication with devices 10 and 11, or by some combination of these. The step of identifying the associated pulse wave may be performed by the processor of the device (e.g. device 11) that measures the selected pulse wave. To do this, the processor (e.g. processor 22) may identify the associated pulse wave from the memory of the other device (e.g. device 10) via communication systems 15 and 25.

Figure 5:
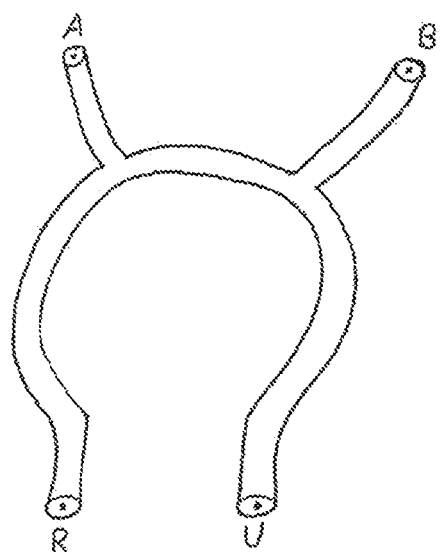
FIG. 5 shows a further simplified diagram of arteries in the hand highlighting particular points for measurements.

FIG. 4 shows an example of a wrist pulse wave 30, followed shortly by two slightly separated digit pulse waves 40 and 50. FIG. 5 shows an arterial arrangement that may produce the pulse waves shown in FIG. 4. FIG. 5 shows a simplified superficial palmar arch, being fed by the radial and ulnar arteries at positions R and U respectively. Positions A and B are exemplary positions in the digital arteries where pulse measurements may be taken (though the measurement device will be located at the surface of the skin). The pulse wave from R will reach point A in the digit shortly before the pulse wave from U does, producing the two slightly separated peaks as shown on the right of FIG. 4. Such measurements allow two separate pulse transit times to be determined, $T_{RA}$ and $T_{UA}$, by comparing the time of arrival of the peak of the pulse wave detected at the wrist with the time of arrival of the peak of the first and second pulse waves detected at position A of the digit respectively. If an equivalent measurement is taken at position B of the digit, two further pulse transit times can be determined, $T_{RB}$ and $T_{UB}$, which are the pulse transit times between the radial and ulnar arteries at the wrist (positions R and U) and position B respectively.

Thus, after performing pulse measurements at the wrist using device 11 and at positions A and B of the digit using device 10, one has determined four pulse transit times. It is useful for the processor to perform one or more validation checks before and after the four pulse transit times are determined. The results of these validation checks may be used to refine and improve previous calculations and assumptions.

For example, it might be determined by a processor that the pulse measurement at one digit only yielded one peak if the two pulse transit times determined at that digit are identical or within a small margin of one another. If it is determined that the measurement at one digit has yielded only one peak, then the expected pulse transit time will be varied until two peaks are detected. This effectively shifts the time window until two peaks are identified in the signal. Similarly, if one of the pulse transit times is determined to be significantly different from the other three, then the time window may be shifted until the four pulse transit times are closer together. If four pulse transit times that are sufficiently close together cannot be found, then this is indicative of a non-standard arterial layout in the hand. The processor will determine that four pulse transit times are insufficiently close together if one of the pulse transit times is not within, for example, if it is more than 1, 2 or 3 standard deviations away from the mean of the pulse transit times.

Once the four pulse transit times are determined, analysis can be performed by the processor in order to determine features of the arterial structure of the hand. A useful operation for the processor to perform is to use the pulse transit times to determine four pulse wave velocities using the relation discussed above, PWV=L/PTT. This can be done by estimating a transit distance for each pulse transit time, i.e. the L in Equation 3. For example, for a system as shown in FIG. 5, the four L values, $L_{RA}$, $L_{UA}$, $L_{RB}$ and $L_{UB}$, are estimates of the length of the arterial path between points R and A, U and A, R and B, and U and B respectively. These estimates may be an average arterial path length for a healthy adult or may use biometric information about the subject to form a better estimate, such as one or more of subject height, weight, age and hand size. Each estimated transit distance (in conjunction with the measure pulse transit time) can then be used to estimate a pulse wave velocity. In an idealised scenario all four pulse wave velocities will be equal, though this is unlikely to be the case in real world measurements.

Analysis of the four pulse wave velocities by the processor can be used to determine information regarding the arterial structure of the hand. Various statistical measures such as one or more of the mean, variance and standard deviation of the pulse wave velocities can be determined. If the processor finds that a pulse wave velocity significantly deviates from the other calculated pulse wave velocities taken during the same set of measurements, e.g. it is more than 1, 2 or 3 standard deviations away from the mean of all of the calculated pulse wave velocities, then this is indicative of an atypical hand arterial structure. As all four pulse wave velocities should be roughly equal, if one of the values has been found to significantly deviate then it is assumed that this value is incorrect due to the associated estimate of L being incorrect. In this case, the average of the other three pulse wave velocities can be assumed to be the "correct" figure and can be used to derive a corrected L value that corresponds to the aberrant pulse wave velocity. In other words, a pulse transit time and an estimate of arterial path length are used by the processor to determine a pulse wave velocity, if this pulse wave velocity significantly deviates from other values then the estimated arterial path length is assumed to be incorrect so other pulse wave velocity values are used to determine a corrected arterial path length.

Estimating the arterial structure of hand by the processor may include estimating the number of arteries in the hand, which arteries are present, the number of and location or arterial branches and the number of arteries present in the wrist.

In the case where the number of arteries present in the wrist is estimated, this estimate can be used by the processor to further refine the measurements taken. For example, wrist PPG measurements may be influenced by the number of wrist arteries present. Data from the wrist PPG measurements may then be normalised with respect to the number of wrist arteries present. For example, if it is determined that three wrist arteries are present, the measured signal may be scaled to a third of the original value.

The processor may also compare the four pulse wave velocities with known values in order to determine whether these pulse wave velocities correspond to a known arterial structure of the hand.

The steps listed above are complicated by the complex branching structure of the hand, resulting in the pertinent measurements not being as clean or easy to isolate as shown in FIG. 4. For example, measurements taken by the sensors 14 and 24 of devices 10 and 11 respectively at locations A and B will be further complicated by the fact that most of the digits are fed by both the superficial and deep palmar arches. One method of obtaining cleaner signals is to use the sensors to measure at certain digits, or at certain locations on certain digits. For example, both the thumb and the thumb side of the index finger are fed only by branches from the deep palmar arch whilst the outside of the little finger is often fed only by a branch from the superficial palmar arch. Thus, the signal quality may be improved by using the sensors to take measurements at the thumb, the thumb side of the index finger, or the outside of the little finger. A more complete picture of the arterial structure of the hand can be built up using measurements from more digits.

After the brachial split below the elbow, blood typically flows down the radial and ulnar arteries concurrently. These two arteries will typically have different lengths and diameters and may also have other differing properties, such as stiffness and the level of 'furring'. Hence, according to Equation 1, the PWV will be different for the wave in each artery. The pulse waves travelling down the radial and ulnar arteries meet in each palmar arch. It is thus apparent that the point at which the pulse waves meet in the palmar arches is dependent on the relative PWV of the waves. The collisions in the palmar arches affect the pulse pressure waves in (amongst other blood vessels) the radial artery of the index finger 7, the common palmar digital arteries 8 and the proper palmar digital arteries 9.

The location and time of the collisions of the pulse waves affects the relative amplitudes of pulse wave velocities in the wrist and the digits and may create reflected waveforms, as described above. The processor may use the time of arrival of a reflected waveform to determine the arterial structure of the hand. For example, in a simplistic model, these collisions can be assumed to occur halfway around the palmar arches, thus spawning waveform features and reflected waveforms that originate at these collision points. The deviation of these waveform features and reflected waveforms from their expected positions allows the location of collision points in the palmar arches to be determined. For example, if the processor detects a waveform feature or reflected waveform at point A before it is detected at point B, then this may be indicative of an asymmetry of the arteries of the hand or arm.

The occlusion of one or more of the radial, ulnar and median arteries during measurement may provide an improved measurement in that a cleaner signal may be obtained. The occlusion of one or more of these arteries also allows the identification of waveform features that originate from a specific arm artery. One or more of the devices 10 and 11 may receive an input from a user indicating that one or more of the radial, ulnar and median arteries is occluded so as to allow the detected waveform features to be identified as originating in a particular arm/wrist artery. Alternatively, one or more of the devices 10 and 11 may indicated to a user that the user should manually occlude/release one or more of the arm/wrist arteries during a measurement. Detection of waveform features taken in measurements immediately after an occluded artery is released can allow the system to determine the length of time it takes for blood flow to return to normal, in a similar manner to Allen's test.

Though the hand is referred to throughout, it should be apparent that the measurements and calculations described below may equally yield information regarding the arterial structure of the wrists and lower arm. Information regarding the arterial structure of the hand may be used to extrapolate information about the wrist and lower arm.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. An apparatus for determining the arterial structure of the hand of a subject, the apparatus comprising:
    a wrist pulse measurement device configured to measure a wrist pulse signal at the wrist of the subject;
    a digit pulse measurement device configured to measure two or more digit pulse signals at a digit of the hand; and
    the apparatus being configured to:
        use an expected pulse transit time to associate the wrist pulse signal with the two or more digit pulse signals, the wrist pulse signal comprising two or more waveform features and the two or more digit pulse signal comprising corresponding two or more waveform features;
        if only one waveform feature is detected in one of the digit pulse signals, vary the expected pulse transit time until two waveform features are detected in each of the two or more digit pulse signals; and
        compare arrival times of the two or more waveform features in the wrist pulse signal at the wrist pulse measurement device and arrival times of the corresponding two or more waveform features in each of the two or more digit pulse signals at the digit pulse measurement device in order to determine a pulse transit time for each of the digit pulse signals, thereby estimating the arterial structure of the hand.

2. An apparatus as claimed in claim 1, wherein the expected pulse transit time is an average time taken for a pulse to travel in two or more arterial paths between a wrist and a digit of a healthy adult.

3. An apparatus as claimed in claim 1, wherein the expected pulse transit time is estimated using one or more of a height, weight, age and hand size of the subject.

4. An apparatus as claimed in claim 1, wherein the wrist pulse measurement device and the digit pulse measurement device are configured to measure the wrist pulse signal and the two or more digit pulse signals with respect to a common time signal.

5. An apparatus as claimed in claim 1, further configured to calculate a pulse wave velocity for each of the two or more waveform features by dividing an estimated arterial path length by the pulse transit time for the each of the two or more waveform features.

6. An apparatus as claimed in claim 5, wherein the estimated arterial path length for the each of the two or more waveform features is an average arterial path length for a healthy adult between a wrist and a digit at which a waveform feature is measured for the healthy adult.

7. An apparatus as claimed in claim 5, wherein the estimated arterial path length for each waveform feature is estimated using one or more of a height, weight, age and hand size of the subject.

8. An apparatus as claimed in claim 5, further configured to determine that the arterial structure is atypical if it is determined that a pulse wave velocity calculated for one of the two or more waveform features deviates from a mean of all calculated pulse wave velocities for all other waveform features of the two or more waveform features by more than 1 standard deviation.

9. An apparatus as claimed in claim 8, further configured to, if it is determined that the pulse wave velocity calculated for one of the two or more waveform features deviates from the mean of all of the calculated pulse wave velocities for all other waveform features, calculate a corrected arterial path length to replace the estimated arterial path length that was used to calculate the pulse wave velocity that deviates from the mean of all of the calculated pulse wave velocities for all other waveform features, wherein the calculation of the corrected arterial path length uses the average of the pulse wave velocities calculated for the other waveform features.

10. An apparatus claimed in claim 5, further configured to compare each of pulse wave velocities with known values to determine whether the pulse wave velocities correspond to a known arterial structure of the hand.

11. An apparatus as claimed in claim 1, further configured to refine the estimate of the arterial structure of the hand using times of arrival of two or more reflected waveforms.

12. An apparatus as claimed in claim 1, further configured to determine a location of waveform collision points in the palmar arches in dependence on a deviation from expected values of the times of arrival of the two or more reflected waveforms spawned by pulse signals colliding in the one or more of the palmar arches.

13. An apparatus as claimed in claim 1, wherein the wrist pulse measurement device comprises one or more of: a photoplethysmography sensor and an electrocardiography sensor.

14. An apparatus as claimed in claim 13, wherein estimating the arterial structure of the hand comprises estimating a number of arteries present in the wrist, and the apparatus is further configured to normalise the wrist pulse signal with respect to the number of arteries present in the wrist.

15. An apparatus as claimed in claim 1, wherein estimating the arterial structure of the hand comprises estimating one or more of: a number of arteries present, which arteries are present, the number of and location of arterial branches.

16. A method of determining the arterial structure of the hand of a subject, the method comprising:
- measuring a wrist pulse signal at the wrist of the subject;
- measuring two or more digit pulse signals, each of the two or more digit pulse signals being measured at a respective digit of the hand;
- using an expected pulse transit time to associate the wrist pulse signal with the two or more digit pulse signals, the wrist pulse signal comprising two or more waveform features and the two or more digit pulse signal comprising corresponding two or more waveform features;
- if only one waveform feature is detected in one of the digit pulse signals, varying the expected pulse transit time until two waveform features are detected in each of the two or more digit pulse signals; and
- comparing arrival times of two or more waveform features in the wrist pulse signal and arrival times of the corresponding waveform features in each of the two or more digit pulse signals in order to determine a pulse transit time for each of the digit pulse signals, thereby estimating the arterial structure of the hand.

17. A non-transitory computer-readable storage medium having instructions encoded thereon that, when executed on a processor, cause the processor to perform a method of determining the arterial structure of the hand of a subject, the method comprising:
- using an expected pulse transit time to associate a wrist pulse signal with two or more digit pulse signals, the wrist pulse signal comprising two or more waveform features and the two or more digit pulse signal comprising corresponding two or more waveform features;
- if only one waveform feature is detected in one of the digit pulse signals, varying the expected pulse transit time until two waveform features are detected in each of the two or more digit pulse signals; and
- comparing arrival times of two or more waveform features in the wrist pulse signal measured at the wrist of the subject and arrival times of the corresponding two or more waveform features in each of two or more digit pulse signals measured at a digit of the hand, in order to determine a pulse transit time for each of the digit pulse signals, thereby estimating the arterial structure of the hand.

* * * * *